(12) United States Patent
Robitaille

(10) Patent No.: US 9,326,885 B2
(45) Date of Patent: May 3, 2016

(54) VALVED NASAL CANNULA

(76) Inventor: Jean-Pierre Robitaille, Gaspe (CA)

( * ) Notice: Subject to any disclaimer, the term of this patent is extended or adjusted under 35 U.S.C. 154(b) by 1508 days.

(21) Appl. No.: 12/301,157

(22) PCT Filed: May 18, 2007

(86) PCT No.: PCT/CA2007/000922
§ 371 (c)(1),
(2), (4) Date: Mar. 16, 2009

(87) PCT Pub. No.: WO2007/134458
PCT Pub. Date: Nov. 29, 2007

(65) Prior Publication Data
US 2009/0308402 A1    Dec. 17, 2009

(30) Foreign Application Priority Data

May 23, 2006   (GB) .................................. 0610171.1

(51) Int. Cl.
*A61F 5/56*    (2006.01)
(52) U.S. Cl.
CPC .......................................... *A61F 5/56* (2013.01)
(58) Field of Classification Search
CPC ........................................................ A61F 5/56
USPC .............. 128/848, 207.18; 602/902; 251/331, 251/335.2; 137/854
See application file for complete search history.

(56) References Cited

U.S. PATENT DOCUMENTS

| 669,098 A | 3/1901 | Overshiner |
| 1,867,478 A | 7/1932 | Stelzner |

(Continued)

FOREIGN PATENT DOCUMENTS

| EP | 1 917 993 A1 | 5/2008 |
| EP | 1917993 A1 * | 5/2008 |

(Continued)

OTHER PUBLICATIONS

International Search Report in International Application No. PCT/CA2007/000922, dated Aug. 14, 2007, 2 pages.

(Continued)

*Primary Examiner* — Victoria J Hicks
(74) *Attorney, Agent, or Firm* — Brinks Gilson & Lione

(57) ABSTRACT

A valved nasal cannula (10) insertable in a nose of an intended user (14) and usable to selectively restrict a flow of air flowing through the valved nasal cannula (10), the nose having a nostril (12) defining a nostril inlet (15) and a nostril vestibule (16) extending inwardly into the nose from the nostril inlet 15), the valved nasal cannula (10) comprising: —a cannula body (18), the cannula body (18) defining a cannula passageway (20) extending therethrough, the cannula passageway (20) defining a passageway longitudinal axis (22), the cannula body (18) also defining a cannula proximal end (28) and a substantially longitudinally opposed cannula distal end (30), the cannula body (18) being, at least in part, insertable in the nostril with the cannula proximal end (28) positioned inside the nostril vestibule (16) substantially spaced apart from the nostril inlet (15) and the cannula distal end (30) positioned substantially adjacent the nostril inlet; —a valve operatively coupled to the cannula body (18) for selectively restricting the flow of air through the cannula passageway (20); and —a protective grid (54), the protective grid (54) extending from the cannula body (18) across the cannula passageway (20), the protective grid (54) being located closer to the cannula proximal end (28) than the valve.

25 Claims, 7 Drawing Sheets

(56) References Cited

U.S. PATENT DOCUMENTS

| | | | |
|---|---|---|---|
| 2,571,906 A | 6/1956 | Irvine | |
| 2,751,906 A | 6/1956 | Irvine | |
| 3,424,152 A | 1/1969 | Kuhlman | |
| 4,120,299 A | 10/1978 | Russo | |
| 4,325,366 A | 4/1982 | Tabor | |
| 4,878,513 A | 11/1989 | Ashby | |
| 5,059,208 A | 10/1991 | Coe | |
| 5,665,104 A | 9/1997 | Lee | |
| 5,775,335 A | 7/1998 | Seal | |
| 5,816,241 A | 10/1998 | Cook | |
| 6,386,197 B1 | 5/2002 | Miller | |
| 6,564,800 B1 | 5/2003 | Olivares | |
| 6,626,172 B1 | 9/2003 | Karow et al. | |
| 6,626,179 B1 | 9/2003 | Pedley | |
| 7,156,099 B1 | 1/2007 | Jenkins | |
| 7,506,649 B2 * | 3/2009 | Doshi et al. | 128/207.18 |
| 7,735,491 B2 | 6/2010 | Doshi et al. | |
| 7,735,492 B2 | 6/2010 | Doshi et al. | |
| 7,775,210 B2 * | 8/2010 | Schobel et al. | 128/207.18 |
| 7,798,148 B2 * | 9/2010 | Doshi et al. | 128/207.18 |
| 7,856,979 B2 * | 12/2010 | Doshi et al. | 128/206.11 |
| 2002/0177871 A1 | 11/2002 | Santin | |
| 2004/0261791 A1 | 12/2004 | Horian | |
| 2006/0150978 A1 | 7/2006 | Doshi et al. | |
| 2006/0150979 A1 | 7/2006 | Doshi et al. | |
| 2007/0175478 A1 * | 8/2007 | Brunst | 128/206.18 |
| 2007/0227542 A1 * | 10/2007 | Kashmakov et al. | 128/206.11 |

FOREIGN PATENT DOCUMENTS

| | | |
|---|---|---|
| FR | 2 210 109 A | 7/1974 |
| FR | 2 610 830 | 8/1988 |
| GB | 2 126 101 A | 3/1984 |
| GB | 2 176 406 A | 12/1986 |
| WO | WO 87/05798 | 10/1987 |
| WO | WO 2004/060438 A2 | 7/2004 |
| WO | WO 2004/060438 A3 | 7/2004 |
| WO | WO 2006/063339 | 6/2006 |
| WO | WO 2007/134458 A1 | 11/2007 |

OTHER PUBLICATIONS

Supplementary European Search Report in European Application No. 07 71 9844, dated Oct. 7, 2009, 7 pages.

* cited by examiner

VALVED NASAL CANNULA

FIELD OF THE INVENTION

The present invention relates to the general field of devices and methods for breathing problems such as snoring and sleep apnea and is particularly concerned with a valved nasal cannula.

BACKGROUND OF THE INVENTION

The prevalence of breathing disorders during sleep, including snoring and sleep apnea, is relatively high. Such disorders are associated with significant morbidity.

The harsh and rough sound known as snoring is typically caused when a person breathes through his or her mouth during sleep in such a manner so as to cause the soft palate and/or uvula to vibrate, but may also occur when the person breathes through his or her nose. In addition to the irritating snoring sound which may cause potential marital stress, it has been suggested that mouth breathing is unhealthy. Indeed, it contributes to the development of gum diseases such as pyorrhoea and also to an unpleasant dry mouth syndrome.

Sleep apnea is a potentially lethal condition characterized by multiple mixed or obstructed apneas during sleep. Symptoms of sleep apnea include repetitive episodes of inordinately loud snoring and excessive daytime sleepiness.

The characteristic snoring pattern noted during sleep apnea is one in which inspiratory snores gradually increase when obstruction of the upper airway develops. A loud, choking inspiratory gasp then occurs as the respiratory efforts succeed in overcoming the occlusion.

The aroused individual subject to sleep apnea is usually aware of neither the breathing difficulty nor of the accompanying body movements that, at times, violently disturb his or her sleep. Typically, a diagnostic study is necessary for an adequate description of the problematic sleep breathing pattern.

Apneic episodes during sleep are typically defined as cessations of air flow at nose and mouth lasting 10 seconds or more. It can be readily documented by so-called poly-somnographic recordings.

There are varying degrees of apnea differentiated by the frequency of periodic breathing cessation episodes during sleep, and also the degree of hypoxia resulting from the related irregular breathing pattern.

When normal breathing is disrupted during sleep, an increased carbon dioxide level and a reduced oxygen level appear in the blood. The sleeping person is then suddenly aroused and gasps for air. This gasping for air is often accompanied by a loud snort.

An increased carbon dioxide level in the blood can cause adverse effects on the vital organs. The heart is usually caused to pump harder and at a higher rate in an effort to compensate for the lack of oxygen. Other organs, such as the kidneys and liver are suddenly confronted with increase blood flow and must adjust to cope with this change. This cycle may be repeated many times during a night's rest and often results in a general lack of proper rest and the restorative benefits thereof.

Some of the health related problems associated with sleep apnea include hypertension, stroke, irregular heartbeat, heart attack as well as the psychogenic conditions from the loss of restful sleep.

It is generally believed that the cause to this condition is a narrowing of the airways while sleeping. This is believed to be caused by a collapse of the tissue structures surrounding the airway. There seems, however, to be no consensus as to what tissue structures the condition should be-attributed to and as to why certain tissue structures close.

There are differing locations and patterns of pharyngeal collapse for each person. In addition to the physical findings and properties which characterize the pharynx in individuals with obstructive sleep apnea such as increased collapsibility, increase compliance, increased resistance and decreased cross-sectional area, the physical properties and spatial relationships of the pharyngeal airway, head and neck, as well as the neuro-muscular integrity of the airway and a mechanism of breathing control must also be considered relevant in their contribution to the mechanism and precipitation of upper airway collapse.

In general, it may be considered that obstructive apnea occurs during sleep when the pharyngeal dilator muscle activity (genioglossus, the infrahyoid muscle and the palatal muscle group) that normally maintain airway potency during inspiration through dilation of the airways, is diminished. When the intraluminal negative pressure of the airway reaches a critical point, the combination of redundant tissues and the loss of pharyngeal muscle tonus cause airway collapse during inspiration. It should, however, be noted that obstruction has also been found to occur during expiration and inspiration.

The prior art is replete with various methods and devices that have been proposed in attempts to cure snoring and sleep apnea. Treatments available for sleep apnea vary from weight loss to surgical interventions to prosthetic devices. Although weight loss is the most desirable approach, few patients are able to comply with their diets and very few can afford to continue the exposure to the symptoms of sleep apnea for extended periods while losing sufficient weight to reduce or cure the disease.

Surgical approaches are only effective in about 50% of cases. They are also invasive, expensive and may produce undesirable side effects.

The most successful prosthetic device has been the nasal continuous positive airway ventilator or pressure known as "CPAP". The advantages of the nasal CPAP system are that it produces immediate relief, is non-invasive and can be used while achieving weight loss, hence eliminating the need for surgery.

The CPAP technique, however, suffers from some important drawbacks. One of the primary drawbacks associated with nasal CPAP has been compliance. While nearly all patients are fitted with nasal CPAP as an initial treatment modality, many cease using the system after a few months. At least three primary factors have been identified as the cause for poor compliance amongst individuals using the CPAP system. One such factor is the lack of perfect fit and discomfort of wearing a nasal mask. The positive pressure of the ventilator flow is often mentioned as another factor. Some patients experience an uncomfortable and annoying sensation of forced air stream in their nose and mouth. Also, dry mouth and throat are often cited as the source of dissatisfaction with the sleep apnea ventilators known as CPAP.

Another type of devices used for treating sleep apnea is a valved nasal cannula insertable in the nostril of an intended user. Such cannulae typically include a body defining a passageway: A valve extends across the passageway and is configured to allow air to flow substantially unaffected into the nose of the intended user, but to restrict any outgoing flow of air so as to provide a backpressure, with the intention of keeping the airways open so as to reduce snoring.

Many such devices have a valve taking the form of a flexible leaflet extending across the passageway and attached to the body at the periphery thereof. This is the case, for example, of some of the nasal cannulae described in U.S. Pat. No. 6,626,179 issued Sep. 30, 2003 to Pedley, and of some of the cannula described in US Patent Application 2006/0150979 of Doshi et al. published Jul. 13, 2006. However, such leaflets may be influenced by gravity as the orientation of the leaflet relatively to its attachment point will influence its dynamic properties. Furthermore, these leaflets present a relatively large lever relatively to their attachment points and therefore have a relatively large response time when transitioning between their "free flowing" configurations to their "backpressure providing" configurations.

The above-referenced US Patent Application 2006/0150979 presents some valved nasal cannulae that alleviate at least in part these problems by having valves that are supported at the center thereof by a frame extending across the passageway. Also, some of the valves presented in this document are supported by the body of the cannula at two diametrically opposed location and fold in two to let air flow upon inspiration by the intended user. These two types of valves however may lead to the valve leaflet sticking to itself or to the relatively flat surfaces of the valve support, which again reduces response time and may even lead to valve malfunction.

Another problem of these valves resides in that if the valve becomes detached from the body of the cannula for any reason, the valve may be aspirated by the user of the valve and block the airways of this user.

Accordingly, there exists a need in the industry for an improved valved nasal cannula. An object of the present invention is therefore to provide an improved valved nasal cannula.

SUMMARY OF THE INVENTION

In a first broad aspect, the invention provides a valved nasal cannula, the valved nasal cannula being insertable in a nose of an intended user and usable to selectively restrict a flow of air flowing through the valved nasal cannula, the nose having a nostril defining a nostril inlet and a nostril vestibule extending inwardly into the nose from the nostril inlet, the valved nasal cannula comprising:

a cannula body, the cannula body defining a cannula passageway extending therethrough, the cannula passageway defining a passageway longitudinal axis, the cannula body also defining a cannula proximal end and a substantially longitudinally opposed cannula distal end, the cannula body being, at least in part, insertable in the nostril with the cannula proximal end positioned inside the nostril vestibule substantially spaced apart from the nostril inlet and the cannula distal end positioned substantially adjacent the nostril inlet;

a valve operatively coupled to the cannula body for selectively restricting the flow of air through the cannula passageway; and a protective grid, the protective grid extending from the cannula body across said cannula passageway, the protective grid being located closer to the cannula proximal end than the valve;

whereby the protective grid increases the safety of the valved nasal cannula by preventing relatively large objects from being inhaled by the intended user while the valved nasal cannula is inserted in the nostril.

Advantages of the present invention include that the proposed valved nasal cannula is adapted to provide a positive pressure in the airway using the breathing of the intended user as a source of positive pressure without the need for an external source of energy and/or compressed air. The proposed cannula is designed so as to be relatively easily insertable and retractable into and from the nasal vestibule portion of the nose of the intended user without requiring manual dexterity.

The protective grid serves, among other purposes, to prevent the valve from obstructing the airways of the intended user should the valve become detached from the cannula body.

Also, the proposed cannula is designed so as to be comfortable once inserted into the nasal vestibule of the intended user. The proposed cannula is designed so as to be substantially fittingly inserted into the nasal vestibule and, in at least some embodiments, to enlarge the latter so as to optimize the breathing passageway.

Also, in some embodiments of the invention, the proposed cannula is designed so as to be resiliently deformable in order to reduce the risk of injury should the nose of the intended wearer be subjected to an impact while housing the proposed cannula.

The proposed cannula may be used for reducing sleep disorder breathing and/or as a breathing exercise as it may be the case for example in Chronic Obstructive Pulmonary Disease (COPD) affecting the inspiratory muscles. In order to exercise the muscles for such a disease (COPD) the cannula is inserted, for a short period of exercise, upside down into the nasal nostril or preferably a special cannula having a reverse configuration would be used. This configuration allows to induce a resistance to air flow during the inspiration phase rather than at the expiration phase consequently the inspiratory muscles will gain in strength.

The proposed cannula may optionally be provided with features such as thermal insulation properties in order to reduce the thermal exchange between the airway and the air flowing therethrough, filtering and/or air moisturizing means, active substance dispensing means for dispensing active substances having a stimulating, therapeutic and/or prophylactic effect.

The proposed device is also designed so as to be manufacturable using conventional forms of manufacturing and conventional materials such as a polymeric resin injecting moulding process using suitable hypo-allergic resins so as to provide a nasal cannula that will be economically feasible, long-lasting and relatively trouble-free in operation.

The proposed nasal cannula is also designed so as to optimize the air flow therethrough.

The proposed nasal cannula is also designed so as to reduce the resistance to air flow during the inspiratory phase of breathing and so as to be substantially silent during use.

Other objects, advantages and features of the present invention will become more apparent upon reading of the following non-restrictive description of preferred embodiments thereof, given by way of example only with reference to the accompanying drawings.

DETAILED DESCRIPTION

Figure 1:
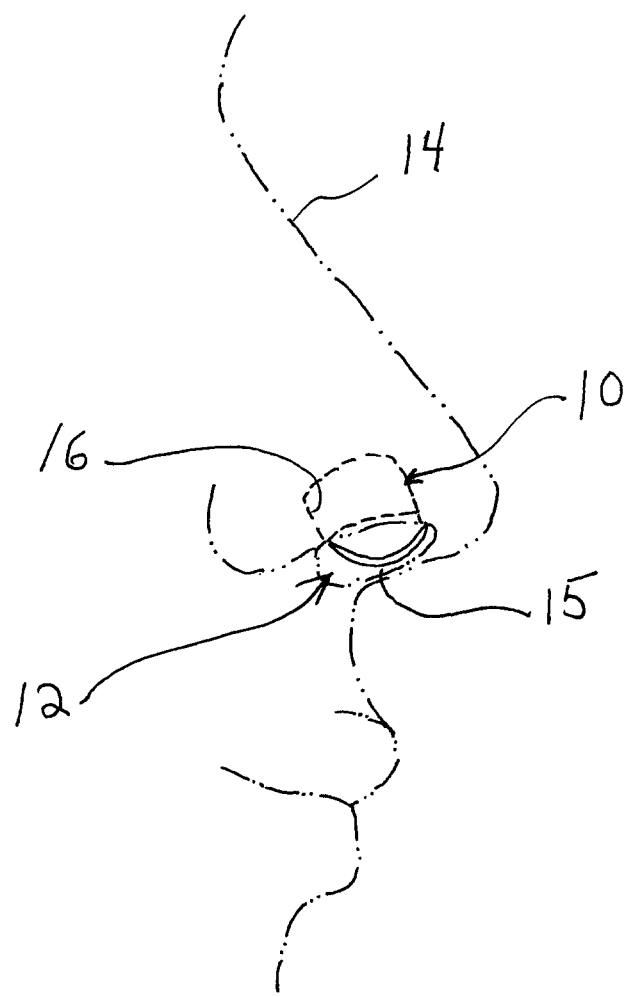
FIG. 1, in a partial elevational view, illustrates a valved nasal cannula in accordance with an embodiment of the present invention, the nasal cannula being shown inserted into the nasal vestibule region of the nose of an intended user, the intended user being shown, in part, in phantom lines.

Referring to FIG. 1, there is shown a valved nasal cannula in accordance with an embodiment of the present invention generally indicated by the reference numeral 10. The nasal cannula 10 is shown inserted in the nostril 12 of an intended user 14 substantially in register with the nasal vestibule 16 of the intended user 14. The valved nasal cannula 10 is insertable in the nose of the intended user 14 and usable to selectively restrict a flow of air flowing through the valved nasal cannula 10. The nostril 12 defines a nostril inlet 15 and a nostril vestibule, part of the nasal vestibule 16, the nostril vestibule extending inwardly into the nose from the nostril inlet 15.

Figure 2:
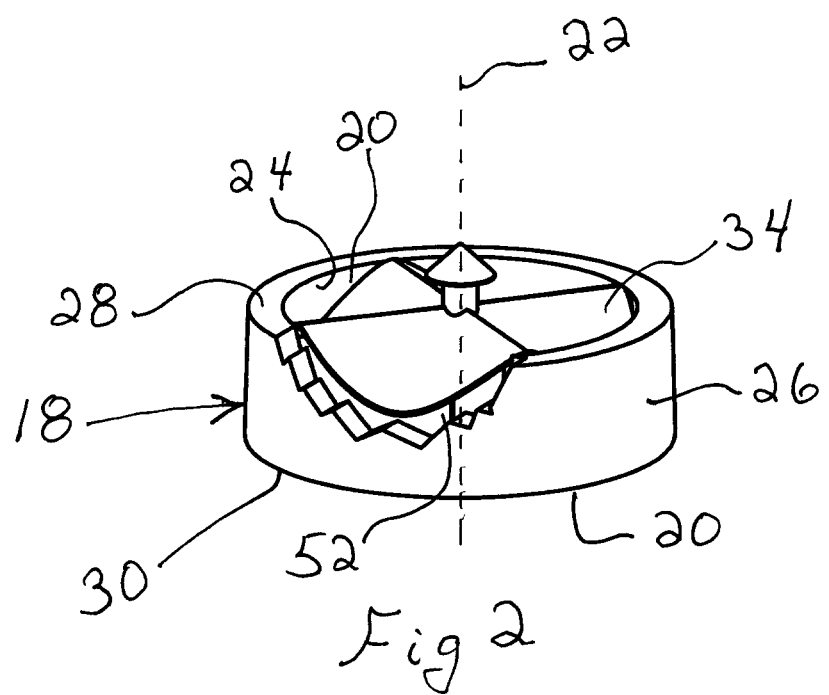
FIG. 2, in a partial perspective view with sections taken out, illustrates a valved nasal cannula in accordance with an embodiment of the present invention.

As illustrated more specifically in FIG. 2, the nasal cannula 10 has a cannula body generally indicated by the reference numeral 18. The cannula body 18 defines a cannula passageway 20 extending therethrough along a passageway longitudinal axis 22.

The cannula body 18 also defines a body inner surface 24 and an opposed body outer surface 26. The cannula body 18 is configured and sized for being substantially snugly fitted in the region of the nasal vestibule 16. The internal tissue of the nasal vestibule 16 is typically considered to be less sensitive to tactile stimulation than downstream nasal tissue and, hence, less susceptible of sending nociceptive signals to the brain upon a foreign body being inserted therein.

The cannula body 18 typically has a substantially frusto-conical configuration defining a cannula proximal end 28 and a longitudinally opposed cannula distal end 30. The cannula body 18 is, at least in part, insertable in the nostril 12 with the cannula proximal end 28 positioned inside the nostril vestibule substantially spaced apart from the nostril inlet 15 and the cannula distal end 30 positioned substantially adjacent the nostril inlet 15. In other words, the cannula proximal end 28 is adapted to be positioned nearer to the sinuses of the intended wearer while the cannula distal end 30 is adapted to be positioned nearer to the inlet of the nostril 12. Typically, the external diameter of the cannula proximal end 28 is smaller than that of the cannula distal end 30. Therefore, in these embodiments, the body outer surface 26 is tapered in a direction leading from the cannula distal end 30 towards the cannula proximal end 28.

Figure 3:
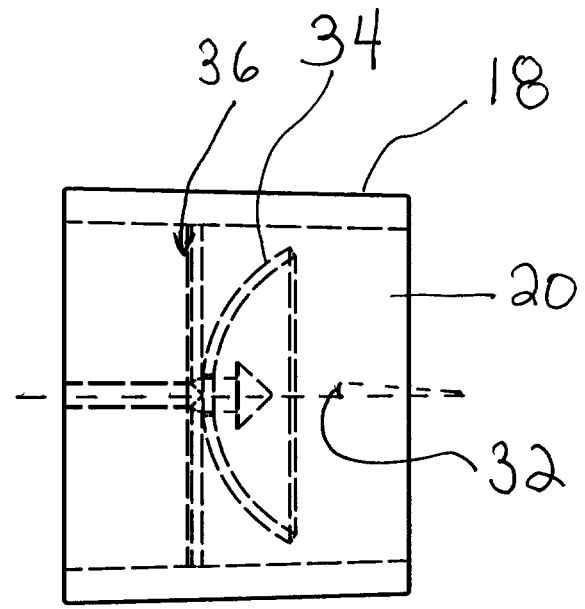
FIG. 3, in a longitudinal cross-sectional view, illustrates some of the features of a valved nasal cannula in accordance with an embodiment of the present invention, the valved nasal cannula being shown with its valve in an opened configuration.

As illustrated more specifically in FIG. 3, the cannula outer surface 26 is angled relative to the passageway longitudinal axis 22 by an outer surface-to-longitudinal axis angle 32.

Throughout the Figures, the outer surface-to-longitudinal axis angle 32 is shown having a substantially constant value of a few degrees. It should, however, be understood that the outer surface-to-longitudinal axis angle 32 could vary without departing from the scope of the present invention. Typically, the cannula body 18 is configured and sized for providing a radial outward pressure so as to slightly increase the size of the nasal vestibule 16.

The outer surface-to-longitudinal axis angle 32, as well as the diameter of the cannula body 18 and its length are typically chosen for a given user in order to ensure a comfortable yet substantially snug fit in the nasal vestibule 16 of the intended user in order to ensure that the cannula body 18 remains in proper alignment therewith.

The substantially frustro-conical configuration of the body outer surface 26 allows for such a comfortable yet snug fit taking into consideration the anatomical configuration of the internal surface of the nasal vestibule 16 since it substantially increases the probability of having a substantially uniform or constant contact with the internal surface of the nasal vestibule 16.

In order to reduce the risks of creating a localized pressure onto the relatively sensitive tissues of the nasal cavity, the body outer surface 26 is typically provided with a substantially smooth texture. Also, the body outer surface 26 is typically provided with a substantially resiliently deformable characteristic. The cannula body 18 may be made out of an integral material having such characteristics or, alternatively, the body outer surface 26 may be coated with a substantially resiliently deformable material.

Typically, the cannula body 18, as a whole, is made out of a substantially resiliently deformable material and provides resiliency so as to be able to temporarily deform upon an impact of a predetermined magnitude being imparted thereon so as to reduce the risk of injury to the internal tissues of the nose of the intended user 14 should an impact be imparted externally on the nose of the intended user 14. More specifically, the cannula body 18 is substantially resiliently deformable between a body undeformed configuration and a body deformed configuration, whereby the cannula body 18 is able to temporarily deform from the body undeformed configuration to the body deformed configuration upon an impact of the predetermined magnitude being imparted thereon.

In at least one embodiment of the invention, the cannula body 18 is made out first of a resiliently deformable material while the body outer surface 26 is coated with a second resiliently deformable material. The characteristics of the first and second resiliently deformable materials may be identical or different without departing from the scope of the present invention.

In some embodiments of the invention, the cannula body 18 and/or the coating on the body external surface 26 is made of an hypo-allergic material such as a latex-free polymeric resin so as to reduce the risk of creating an allergic reaction once inserted into the nose of the intended user.

Also, in at least some embodiments of the invention, the cannula body 18 and/or the coating on the body external surface 26 is made out of a heat insulating material so as to reduce the heat transfer between the mucosa of the nose of the intended user and the air flowing through the nasal cannula. The reduced heat transfer may allow for cooler air to reach internal tissues so as to reduce oedema thereof.

The nasal cannula 10 further includes a valve, or airflow restrictor, for selectively restricting the flow of air through the cannula passageway 20. The valve is operatively coupled to the cannula body for selectively restricting the flow of air through the cannula passageway. Typically, the valve is a diaphragm-type valve and is positioned in the cannula passageway 20 substantially spaced apart from both the cannula proximal and distal ends 28 and 30, although other types and positions of the valve could be used without departing from the scope of the present invention.

Figure 4:
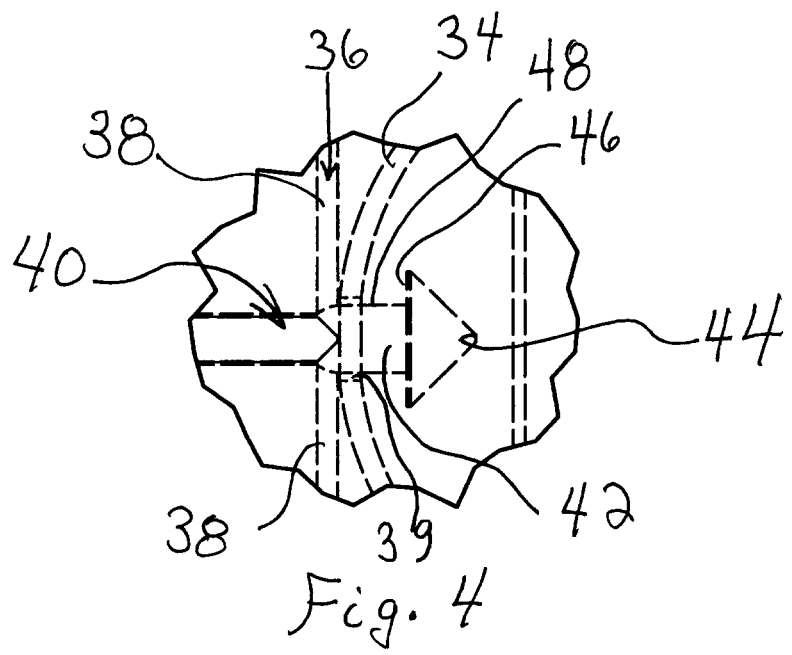
FIG. 4, in a partial longitudinal cross-sectional view with sections taken out, illustrates part of a valved nasal cannula in accordance with an embodiment of the present invention, the nasal cannula being shown with its valve in an opened configuration.

In the embodiments shown throughout the drawings, and as seen for example in FIGS. 3 and 4, the valve includes a diaphragm disc 34 made out of a resiliently deformable material. The diaphragm disc 34 is mounted on a diaphragm frame generally indicated by the reference numeral 36 for extending across the cannula passageway 20.

Figure 5:
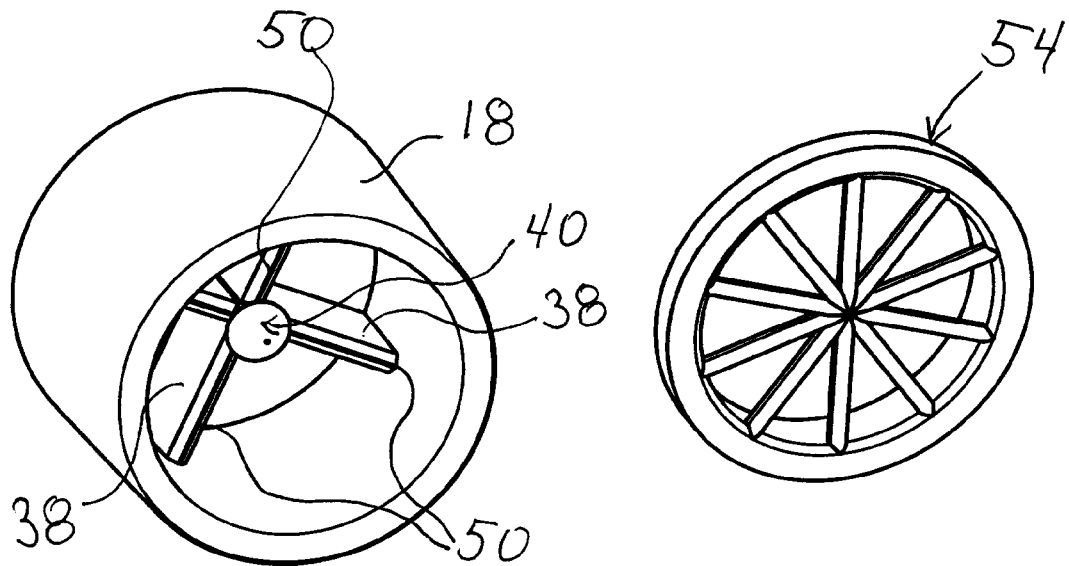
FIG. 5, in a partially exploded perspective view, illustrates a valved nasal cannula in accordance with an embodiment of the present invention.

As illustrated more specifically in FIG. 5, the diaphragm frame 36 includes at least one and preferably an array of supporting ribs or spokes 38 extending across the cannula passageway 20. Typically, the spokes 38 extend substantially radially from a substantially centrally disposed hub 40 to the body inner surface 24, and therefore extend substantially diametrically across the cannula passageway 20.

As illustrated more specifically in FIG. 4, the hub 40 typically includes an anchoring portion for anchoring a central portion of the diaphragm disc 34. The anchoring portion may take any suitable form. In the embodiment shown throughout the Figures, the anchoring portion includes an anchoring stem 42 extending substantially longitudinally in the cannula passageway 20 from a location substantially at the intersection of the spokes 38. A retaining prong 44 extends substantially longitudinally from the anchoring stem 42, the retaining prong 44 having a radius larger than a radius of the anchoring stem 42. Typically, although by no means exclusively, the retaining prong 44 has a substantially inverted conical configuration defining an annular retaining lip 46. The retaining lip 46 and the adjacent surface of the spokes 38 define a disc-receiving spacing 48 therebetween.

The diaphragm disc 34 is provided with a corresponding a mounting aperture 39 extending therethrough, the mounting aperture 39 having a radius substantially smaller than the radius of the retaining stem 42, and more specifically of the retaining lip 46. The resilient nature of the diaphragm disc 34 allows the diaphragm disc 34 to be stretched radially so as to allow the mounting aperture 39 to be fitted over the retaining prong 44 into the disc-receiving spacing 48. This configuration of the valve allows to replace the diaphragm disc 34 should the diaphragm disc 34 become damaged, or should the needs of the intended user 14 change. For example, the diaphragm disc 34 could be exchanged for a diaphragm disc 34 having a different rigidity, or for a diaphragm disc 34 including a substance able to diffuse into the airflow passing thereby.

The diaphragm disc 34 is located closer to the body proximal end 28 than the diaphragm frame 36. Therefore, the resilient nature of the diaphragm disc 34 allows the latter to bend when subjected to a pressure imparted thereon. Typically, during the inspiration phase of breathing, the disc deforms substantially freely from a substantially flat closed configuration wherein it rests on the spokes 38 to an opened configuration shown in FIG. 3 wherein it allows the flow of air through the cannula passageway 20, particularly about the periphery thereof.

In some embodiments of the invention, the diaphragm frame 36 and the diaphragm disc 34 have dimensions, configurations and deformation properties such that a substantially constant backpressure is exerted by the diaphragm disc 34 upon the intended user expiring air from the cannula proximal end 28 towards the cannula distal end 30 for a predetermined range of expiration flow rate. For example, the substantially constant backpressure is from about 0.1 cm $H_2O$ to about 100 cm $H_2O$, and in some embodiments from about 0.5 cm $H_2O$ to about 20 cm $H_2O$. In some embodiments of the invention, the predetermined range of expiration flow rate is from about 0.5 L/min to about 60 L/min, and in some embodiments, from about 10 L/min to about 40 L/min.

Referring back to FIG. 5, there is shown that the proximal end of the ribs 38 adapted to contact the diaphragm disc 34 typically have a substantially pointed configuration defining an abutment apex 50. The use of a relatively small contact surface between the spokes 38 and the diaphragm disc 34 is adapted to reduce adherence therebetween and, hence, to reduce resistance or inertia to the initial flow of air during the inspiration phase of breathing.

The number of spokes 38, their thickness, the spacing therebetween, and the thickness and material of the diaphragm disc 34 are typically calibrated so as to provide a predetermined resistance to the flow of air during the expiration phase of breathing. During the expiration phase of breathing, the diaphragm disc 34 is pushed back from its opened configuration shown in FIG. 3 to the closed configuration wherein it abuts against the contacting apex 50 of the spokes 38.

Upon the pressure building up in the airway upstream from the nasal cannula 10 as a result of the air being blocked from flowing through the nasal passageway during the initial stage of the expiration phase of breathing, the internal pressure will eventually cause the diaphragm disc 34 to deform into a restricting configuration shown in FIG. 2 wherein moveable portions of the diaphragm disc 34 are deflected between the spokes 38 hence creating peripheral passageways 52 through which the air may be expelled out of the nose of the intended user.

Hence, by using a substantially centrally anchored diaphragm disc 34 adapted to deform substantially about its periphery, a substantially constant resistance to air flow is provided during both the inspiration and expiration phases of breathing mainly because of the resilient nature of the diaphragm disc 34. The resistance to air flow during the inspiratory phase will be less than the one during the expiratory phase of breathing. Furthermore, the delay of action of the valve is relatively short. Also, since the air will flow substantially peripherally, the air is distributed along the internal tissues of the nose hence improving the naturally occurring of heat exchange and humidification of the air flowing there through. Also, the diaphragm disc deflecting substantially peripherally and abutting against relatively small contact surfaces will have a tendency to be substantially silent and to have a relatively fast response time when the intended user switches between inspiration and expiration breathing.

Figure 6:
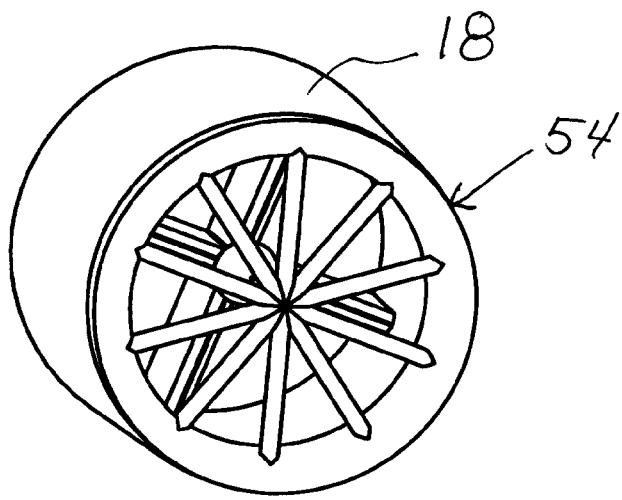
FIG. 6, in a perspective view, illustrates the valved nasal cannula shown in FIG. 5.

In some embodiments of the invention, as seen in FIGS. 5 and 6, the nasal cannula 10 is provided with a protective grid 54 or other suitable retaining means for ensuring that the diaphragm disc 34 remains within the cannula body 18 should the diaphragm disc 34 be unvoluntarily released from its anchoring means. The protective grid extends from the cannula body 18 and extends across the cannula passageway 20. The protective grid 54 is located closer to the cannula proximal end 28 than the valve, and in some embodiments, is located substantially adjacent the cannula proximal end 28. The protective grid 54 also increases the safety of the valved nasal cannula 10 by preventing relatively large objects from being inhaled by the intended user while the valved nasal cannula is inserted in the nostril 12.

In addition to, or independently from the valve, the nasal cannula 10 may be provided with a filtering medium and/or an air treating medium. For example, the nasal cannula 10 may be provided with an HEPA filter located within the cannula body 18 or any other suitable filter. The nasal cannula 10 may also be provided with a heat and/or humidity exchanger. The nasal cannula 10 may also be provided with a material mounted therein for dispensing a pharmaceutically active substance, an air treatment substance or any other suitable substance adapted to be activated by the breathing of the user and/or intrinsically active.

Figure 7:
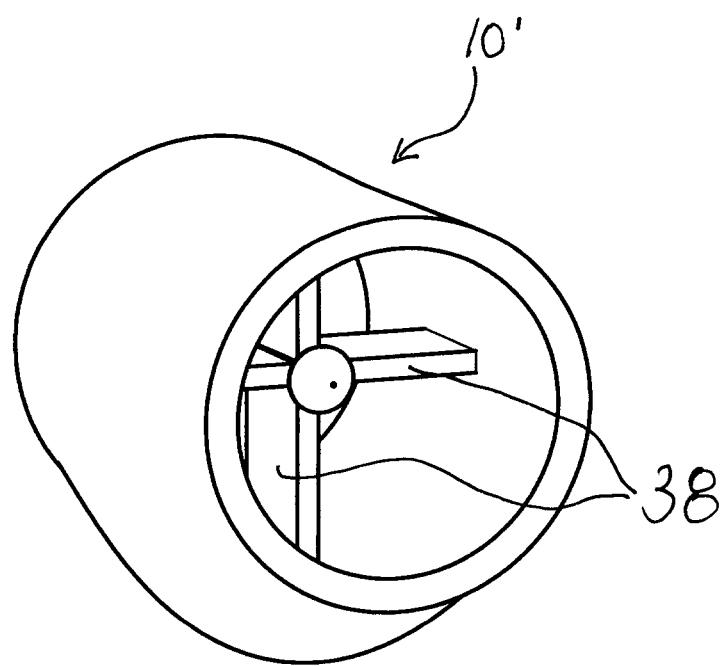
FIG. 7, in a top view, illustrates a valved nasal cannula in accordance with another embodiment of the present invention.

As seen in FIG. 7, the nasal cannula 10' is not necessarily frustro-conical and may present a substantially asymmetric configuration that better conforms to the shape of the nose of the intended user.

Figure 8:
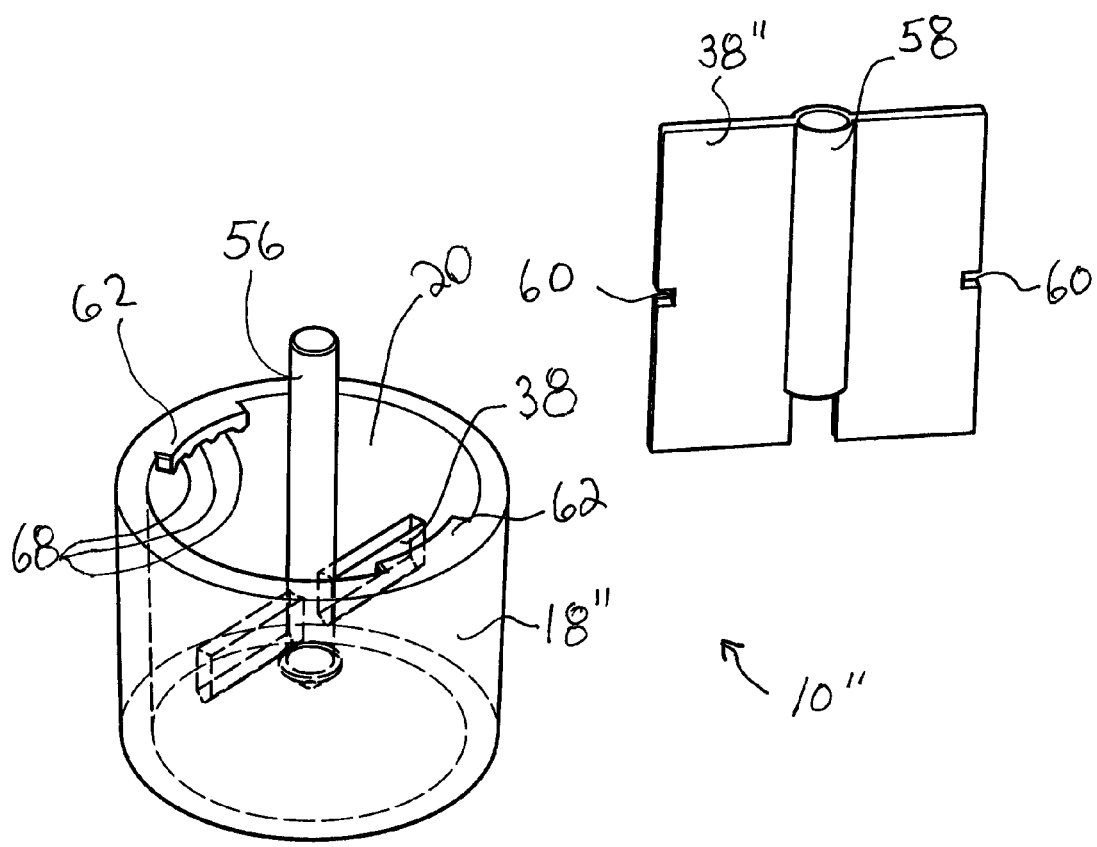
FIG. 8, in a partially exploded perspective view, illustrates a valved nasal cannula in accordance with yet another embodiment of the present invention.

As seen in FIG. 8, a valved nasal cannula 10" in accordance with an alternative embodiment of the invention includes a fixed spoke 38 extending substantially diametrically across the cannula passageway 20 and a mobile spoke 38", the mobile spoke 38" extending substantially diametrically across the cannula passageway 20 and being operatively coupled to the cannula body 18" and to the fixed spoke 38 so as to be rotatable about the passageway longitudinal axis relatively thereto. In these embodiments, for example, the cannula body 18" is substantially cylindrical. The mobile spoke 38", by being angled at a variable angle relatively to the fixed spoke 38, thereby influencing the deformation of the diaphragm disc 34 (not shown in FIG. 8) so as to adjust the backpressure produced by the cannula 10".

Mounting of the mobile spoke 38" may be achieved by having a mounting shaft 56 extending substantially longitudinally from the center of the fixed spoke 38. The mobile spoke 38" is mounted to a substantially longitudinally extending sleeve 58 mounted onto the mounting shaft 56. The mobile spoke 38" defines notches 60 extending substantially radially inwardly thereinto. The cannula body 18" defines substantially radially inwardly extending ledges 62 located so as to engage the notches 60. The ledges 62 define recesses 68 for receiving the notches 60 at circumferentially spaced apart locations, thereby allowing to adjust in discrete steps the position of the mobile spoke 38" relatively to the fixed spoke 38.

Figure 9:
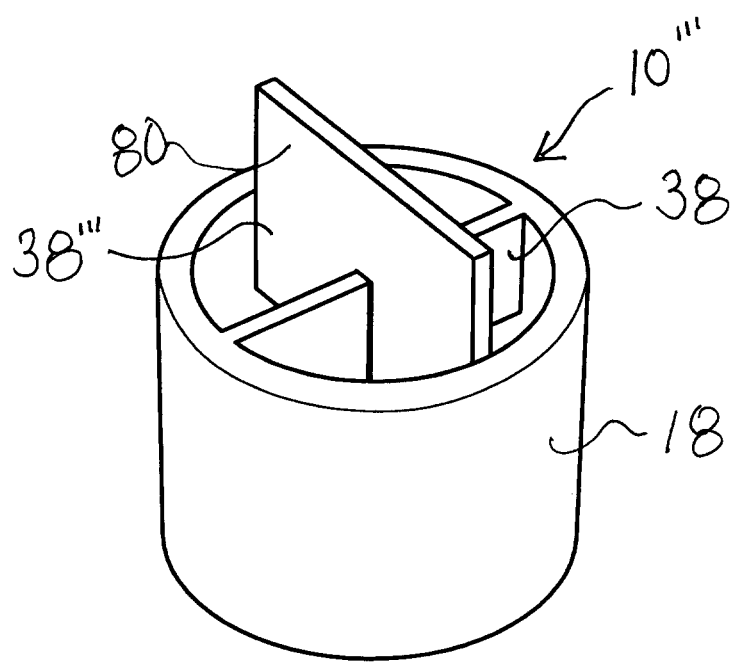
FIG. 9, in a perspective view, illustrates the valved nasal cannula having a prehensile protrusion.

In some embodiments of the invention, as illustrated in FIG. 9 the nasal cannula 10''' is provided with a prehensile protrusion 80 of spoke 38''' which provides a grabbing mean for easily removing the nasal cannula 10''' out of the nostril vestibule.

Although the present invention has been described hereinabove by way of preferred embodiments thereof, it can be modified, without departing from the spirit and nature of the subject invention as defined in the appended claims.

What is claimed is:

1. A valved nasal cannula, said valved nasal cannula being insertable in a nose of an intended user and usable to selectively restrict a flow of air flowing through said valved nasal cannula, said nose having a nostril defining a nostril inlet and a nostril vestibule extending inwardly into said nose from said nostril inlet, said valved nasal cannula comprising:

a cannula body, said cannula body defining a cannula passageway extending therethrough, said cannula passageway defining a passageway longitudinal axis, said cannula body also defining a cannula proximal end and a substantially longitudinally opposed cannula distal end, said cannula body being, at least in part, insertable in said nostril with said cannula proximal end positioned inside said nostril vestibule substantially spaced apart from said nostril inlet and said cannula distal end positioned substantially adjacent said nostril inlet;

a valve operatively coupled to said cannula body for allowing said flow of air through said cannula passageway during an inspiration phase and selectively restricting said flow of air through said cannula passageway during an expiratory phase, wherein said valve comprises a diaphragm made out of a substantially resiliently deformable material and a diaphragm frame extending across said cannula passageway, wherein said diaphragm frame includes a first spoke extending substantially diametrically across said cannula passageway, and a second spoke extending substantially diametrically across said cannula passageway, wherein said second spoke is rotatable about said passageway longitudinal axis relative to said first spoke such that a spacing between said first spoke and said second spoke is varied, and wherein said diaphragm extends substantially across said cannula passageway and is deformable into said spacing between said first and second spokes; and a protective grid, said protective grid extending from said cannula body across said cannula passageway, said protective grid being located closer to said cannula proximal end than an entirety of said valve;

whereby said protective grid increases the safety of said valved nasal cannula by preventing relatively large objects from being inhaled by said intended user while said valved nasal cannula is inserted in said nostril.

2. A valved nasal cannula as defined in claim 1, wherein said diaphragm comprises a disc.

3. A valved nasal cannula as defined in claim 2, wherein said diaphragm frame and said diaphragm disc have dimensions, configurations and deformation properties such that a substantially constant backpressure is exerted by said diaphragm disc upon said intended user expiring air from said cannula proximal end towards said cannula distal end for a predetermined range of expiration flow rate.

4. A valved nasal cannula as defined in claim 3, wherein said substantially constant backpressure is from about 0.1 cm $H_2O$ to about 100 cm $H_2O$.

5. A valved nasal cannula as defined in claim 3, wherein said substantially constant backpressure is from about 0.5 cm $H_2O$ to about 20 cm $H_2O$.

6. A valved nasal cannula as defined in claim 3, wherein said predetermined range of expiration flow rate is from about 0.5 L/min to about 60 L/min.

7. A valved nasal cannula as defined in claim 3, wherein said predetermined range of expiration flow rate is from about 10 L/min to about 40 L/min.

8. A valved nasal cannula as defined in claim 2, wherein said diaphragm frame defines a hub, said hub being substantially centrally disposed relatively to said cannula passageway, said hub defining an anchoring portion, said diaphragm disc being anchored to said anchoring portion.

9. A valved nasal cannula as defined in claim 8, wherein said anchoring portion includes an anchoring stem extending substantially longitudinally in said cannula passageway from said first spoke and a retaining prong extending substantially longitudinally from said anchoring stem, said retaining prong having a radius larger than a radius of said anchoring stem;

said diaphragm disc defines a mounting aperture extending therethrough, said mounting aperture having a radius substantially smaller than said radius of said retaining prong;

said anchoring stem extends through said mounting aperture.

10. A valved nasal cannula as defined in claim 2, wherein said diaphragm disc is located closer to said cannula proximal end than said diaphragm frame.

11. A valved nasal cannula as defined in claim 2, wherein said first spoke has a substantially pointed configuration in a direction leading towards said cannula proximal end.

12. A valved nasal cannula as defined in claim 1, wherein said cannula body defines a body outer surface, said body outer surface being tapered in a direction leading from said cannula distal end towards said cannula proximal end.

13. A valved nasal cannula as defined in claim 12, wherein said body outer surface is substantially frustro-conical.

14. A valved nasal cannula as defined in claim 1, wherein said protective grid is located substantially adjacent said cannula proximal end.

15. A valved nasal cannula as defined in claim 1, wherein said cannula body is substantially resiliently deformable between a body undeformed configuration and a body deformed configuration, whereby said cannula body is able to temporarily deform from said body undeformed configuration to said body deformed configuration upon an impact of a predetermined magnitude being imparted thereon.

16. A valved nasal cannula as defined in claim 1, wherein said valve is positioned in said cannula passageway substantially spaced apart from both said cannula proximal and distal ends.

17. A valved nasal cannula as defined in claim 1, wherein said cannula body defines a body outer surface, said body outer surface being provided with a substantially smooth texture.

18. A valved nasal cannula as defined in claim 1, wherein said cannula body being substantially hypo-allergic.

19. A valved nasal cannula as defined in claim 1, wherein said cannula body is substantially thermally insulating.

20. A valved nasal cannula as defined in claim 1, further comprising a filtering medium or an air treating medium located within said cannula body.

21. A valved nasal cannula as defined in claim 1 wherein said cannula body defines an outer surface, said outer surface being substantially cylindrical.

22. A nasal cannula insertable in a nose of an intended user and usable to restrict a flow of air flowing through said nasal cannula, said nose having a nostril defining a nostril inlet and a nostril vestibule extending inwardly into said nose from said nostril inlet, said nasal cannula comprising:
- a cannula body, said cannula body defining a cannula passageway extending therethrough, said cannula passageway defining a passageway longitudinal axis, said cannula body also defining a cannula proximal end and a substantially longitudinally opposed cannula distal end, said cannula body being, at least in part, insertable in said nostril with said cannula proximal end positioned inside said nostril vestibule substantially spaced apart from said nostril inlet and said cannula distal end positioned substantially adjacent said nostril inlet;
- an airflow restrictor operatively coupled to said cannula body for allowing said flow of air through said cannula passageway during an inspiration phase and restricting said flow of air through said cannula passageway during an expiratory phase, said airflow restrictor comprising a moveable portion moveable relative to said cannula body;
- a frame coupled to said cannula body and comprising a first rib moveable relative to a second rib, wherein a spacing between said first and second ribs is variable, wherein said moveable portion of said airflow restrictor is deformable into said spacing between said first and second ribs;

and
- a protective grid extending from said cannula body across said cannula passageway, said protective grid being located closer to said cannula proximal end than an entirety of said moveable portion of said airflow restrictor.

23. The nasal cannula of claim 22 wherein said moveable portion of said airflow restrictor comprises a valve.

24. The nasal cannula of claim 23 wherein said valve comprises a diaphragm disc.

25. The nasal cannula of claim 22 wherein said first rib is rotatable relative to said second rib about said passageway longitudinal axis.

* * * * *